United States Patent
Bianchi et al.

[11] Patent Number: 5,332,674
[45] Date of Patent: Jul. 26, 1994

[54] PROCESS FOR PREPARING (R) AND (S)-1,2-ISOPROPYLIDENEGLYCEROL BY CRYSTALLIZING RACEMIC BENZOYL ESTER

[75] Inventors: Daniele Bianchi, Milan; Aldo Bosetti, Vercelli; Pietro Cesti, Trecate; Paolo Golini, Turbigo; Carlo Pina, Milan, all of Italy

[73] Assignee: Ministero Dell'Universita' E Della Ricerca Scientifica E Tecnologica, Rome, Italy

[21] Appl. No.: 16,882

[22] Filed: Feb. 12, 1993

[30] Foreign Application Priority Data

Feb. 17, 1992 [IT] Italy ............... MI92 A 000331

[51] Int. Cl.$^5$ ............................................. C12P 41/00
[52] U.S. Cl. ................................... 435/280; 23/296
[58] Field of Search ........................... 435/280; 23/296

[56] References Cited

U.S. PATENT DOCUMENTS 4,957,868  9/1990  Yushina et al. ................... 435/288

FOREIGN PATENT DOCUMENTS 0244912  11/1987  European Pat. Off. .

OTHER PUBLICATIONS

Chemical Abstracts, AN-57587m, vol. 111, No. 7, Aug. 14, 1989, F. Aragozzini, et al., "Enantioselective Microbial Reduction of Monoesters of 1,3-Dihydroxypropanone: Synthesis of (S)-And (R)-1,2-O=Isopropylideneglycerol".

Chemical Abstracts, AN-181855y, vol. 114, No. 19, May 13, 1991, F. Aragozzini, et al., "Enantioselective Hydrolysis of Benzoyl 1,2-O-Isopropylideneglycerol by Bacillus Coagulans".

*Primary Examiner*—Douglas W. Robinson
*Assistant Examiner*—Sandra Saucier
*Attorney, Agent, or Firm*—Oblon, Spivak, McClelland, Maier & Neustadt

[57] ABSTRACT

A process is described for separating the optical isomers of 1,2-isopropylideneglycerol, of formula (I), comprising partially stereoselective enzymatic hydrolysis of 1,2-isopropylideneglycerol benzoyl ester (II) catalyzed by a free or immobilized lipase, the hydrolysis being conducted in the presence of a cosolvent and followed by crystallization enabling crystals of (II) in raceme form and mother liquor containing (II) in the form of the pure enantiomer to be selectively obtained.

The compound (I) is widely used industrially as an intermediate in the synthesis of chiral drugs such as (R)-(−)-carnitine, (S)-beta-blockers, (S)-antiviral agents, analgesic drugs etc.

16 Claims, No Drawings

PROCESS FOR PREPARING (R) AND (S)-1,2-ISOPROPYLIDENEGLYCEROL BY CRYSTALLIZING RACEMIC BENZOYL ESTER

This invention relates to a process for separating the optical isomers of 1,2-isopropylideneglycerol, of formula (I):

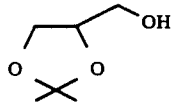

More specifically, the invention relates to enzymatic hydrolysis of the corresponding ester of 1,2-isopropylideneglycerol conducted in the presence of a cosolvent and followed by crystallization. Attempts at resolution of the optical isomers of the alcohol of formula (I) have already been made.

In this respect, reference can be made to an article in *J. Org. Chem.* 43, 4876, 1978, which uses a chemical process involving oxidation of D-mannitol.

This is the currently used synthesis method, however it has the drawback of using lead tetraacetate as oxidizing agent, this being highly toxic and costly.

A process involving stereoselective microbiological oxidation of raceme 1,2-isopropylideneglycerol [hereinafter known as (R,S)-(I)] to give its dextrorotatory form [hereinafter known as (R)-(I)] and the corresponding carboxylic acid in the dextrorotatory form (R), equivalent to the levorotatory form of the alcohol [known hereinafter as (S)-(I)] is described in European patent application 244,912.

The drawback of this method is that it directly provides the (R) isomer of (I), which is that of lesser applicational interest. Access to the (S) isomer is possible only by reducing the corresponding (R) acid with hydrides, this being a reaction difficult to apply at the industrial level.

Finally, Italian patent 1,217,669 describes a process involving stereoselective microbiological hydrolysis of the benzoyl ester of raceme isopropylideneglycerol to give (S)-(I) and (S)-(II), corresponding to (R)-(I).

This method has the typical drawbacks of reactions conducted with whole cells, such as high dilution and the difficulty of recovering the products from the cell suspension.

The applicant has now found that it is possible to obviate the aforesaid drawbacks of the known art by separating the optical isomers of 1,2-isopropylideneglycerol by an enzymatic process using very simple low-cost reagents and reaction steps, to achieve high yields of pure enantiomers.

The present invention therefore provides a process for separating the optical isomers of 1,2-isopropylideneglycerol, of formula (I):

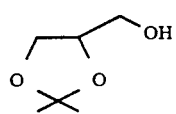

comprising partially stereoselective enzymatic hydrolysis of 1,2-isopropylideneglycerol benzoyl ester, of formula (II):

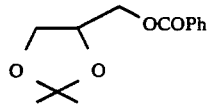

catalyzed by a free or immobilized lipase and conducted in the presence of a cosolvent; the mixture obtained in this manner is separated and the individual compounds are subjected to crystallization from which crystals of (II) in raceme form and mother liquor containing (II) in the form of the pure enantiomer are selectively obtained.

It is particularly surprising to find that the ester of formula (II) is liquid if in the form of the pure enantiomer, but crystallizes if in the raceme form.

This is in total contradiction to previous knowledge. For instance, an article appearing in "Chimica Oggi" of July-August 1991 ("Crystallization techniques for the industrial synthesis of pure enantiomers") states clearly that the pure enantiomers are generally in crystalline form.

By utilizing this property of the ester of formula (II) it is therefore possible, starting from a mixture of enantiomers of the same ester enriched with one of the two isomers, to separate the raceme fraction from the excess of the more abundant isomer. This method is applicable only in the case of the ester of formula (II). In this respect, other esters tested by the applicant containing different acyl groups, such as acetates, butyrates, phenylacetates etc., are liquid both in raceme form and in optically pure form.

The solvents used for the crystallization are $C_5$–$C_8$ aliphatic hydrocarbons, hexane being preferred. If more polar solvents are used, the racemate also dissolves leading to obvious separation difficulty between the racemate and the pure enantiomers.

The crystallization is conducted by dispersing the ester of formula (II) in the solvent and cooling to $-24°$ C. for 24 hours. In practice an ester (II):solvent weight ratio of between 1:4 and 1:1, and preferably 1:2, is used.

To obtain a mixture enriched with the ester of formula (II), the process of the present invention uses enzymatic hydrolysis of the ester, catalyzed by free or immobilized lipase in the presence of a cosolvent.

If operating with a free lipase, the enzymatic hydrolysis is conducted by adding the raceme ester (R,S)-(II), dissolved in the cosolvent, to a buffered solution of the enzyme.

If the lipase is immobilized within a hollow fibre apparatus, this is provided with two inlets, namely an upper inlet and an upper-side inlet, or the buffer solution and for the raceme ester (R,S)-(II) in solution in the cosolvent respectively, and with two outlets, namely a lower outlet and a lower-side outlet, for (S)-(I) in aqueous solution and for (S)-(II) in solution in the cosolvent respectively.

On halting the reaction at 50% conversion, the optical purity of the alcohol (S)-(I), i.e. the reaction product, and of the unreacted ester (S)-(II) are equal at $\leq 60\%$.

(S)-(I) can be re-esterified chemically to give (R)-(II) and then used in the crystallization step. The raceme ester (R,S)-(II), the by-product of the crystallization, can be recycled to the enzymatic hydrolysis reaction.

The entire process of the present invention is better exemplified in Scheme 1.

The cosolvent used has the effect of considerably improving the hydrolysis stereoselectivity.

Linear or branched $C_2$-$C_5$ aliphatic ethers, of which diisopropylether or methyl tert-butyl ether is preferred, or heterocyclic ethers, of which dioxane or tetrahydrofuran is preferred, have proved particularly suitable as cosolvents.

The quantity of cosolvent used can vary from 5 to 50% v/v and preferably between 10 and 25% v/v with respect to the buffer solution.

The buffer solution used is preferably phosphate buffer. The pH of the buffer solution used is between 6 and 8, and preferably 7.

The enzymatic hydrolysis reaction is conducted at a temperature of between 15° and 40° C. and preferably between 25° and 35° C.

The substrate (II) is used in a concentration of between 1 and 10% by weight, and preferably 5%.

The enzyme is used in a weight ratio to the substrate (II) of between 1/100 and 1/1, depending on the type of enzyme used. In particular, the lipase Amano PS from *Pseudomonas cepacea* (supplied by Amano Pharmaceutical Co. Ltd., Japan) and the lipase OF from *Candida cylindracea* (supplied by the Sankyo Company Ltd., Japan) have proved active on the substrate (II).

Finally, the esters (R)-(II) and (S)-(II), in the form of pure enantiomers, can be transformed into the alcohols (S)-(I) and (R)-(I) respectively using known methods such as alkaline hydrolysis with methanol in the presence of NaOH or KOH, or alcoholysis, without changes in optical purity occurring.

The alcohols (S)-(I) and (R)-(I) are widely used industrially as intermediates in the synthesis of chiral drugs such as (R)-(−)-carnitine, (S)-beta-blockers, (S)-antiviral agents, analgesic drugs etc.

The invention is further described by the following examples, which are provided by way of non-limiting illustration.

EXAMPLE 1 a) hydrolysis of (R,S)-(II) with PS lipase in buffer solution 20 g of (R,S)-benzoyl-1,2-isopropylideneglycerol (II) were added to a solution of 15 g of Amano PS lipase in 400 ml of pH 7, 0.01N phosphate buffer at 30° C.

The suspension was vigorously agitated, maintaining the pH constant by adding a 2N NaOH solution.

Samples of the reaction mixture were periodically withdrawn and analyzed by HPLC (high pressure liquid chromatography), using a column with a chiral stationary phase (column: Chiracel Daicel OB), and 9/1 hexane/isopropanol as eluent at a flow of 0.8 ml/min.

After 8 hours the reaction was halted at 50% conversion. The unreacted ester (II) was separated from the reaction mixture by extraction with hexane.

The organic phase was dried over sodium sulphate and evaporated under reduced pressure, to give 9.5 g of (S)-(−)-(II), $[\alpha]_D^{25} = -3.3°$ (C=1, CHCl$_3$), with 38% excess enantiomer (e.e.).

The alcohol (I) was recovered from the aqueous phase after saturating with NaCl followed by extraction with ethyl acetate. After drying over sodium sulphate and evaporating the solvent, 5.2 g of (S)-(+)-(I) are obtained, with $[\alpha]_D^{25} = +4.5°$ (C=1, MeOH), and e.e. = 39%.

b) Crystallization of (II)

9.5 g of (S)-(−)-(II) (e.e. = 38%) were added to 19 ml of hexane and the mixture maintained at −24° C.

After 24 hours 5.6 g of solid phase separate, consisting of the, substantially raceme ester (II), $[\alpha]_D^{25} = -0.5°$ (C=1, CHCl$_3$). From the supernatant, after evaporating the hexane under reduced pressure, 3.6 g of (S)-(−)-(II) are obtained, with $[\alpha]_D^{25} = -8.1°$ (C=1, CHCl$_3$), e.e. = 94%, yield = 18%.

5.2 g of alcohol (S)-(+)-(I) (e.e. = 39%) and 6.7 ml of triethylamine were dissolved in 50 ml of CH$_2$Cl$_2$.

5.5 ml of benzoyl chloride dissolved in 10 ml of CH$_2$Cl$_2$ were dripped into this solution.

After filtering off the triethylamine hydrochloride the supernatant was washed with water, dried with sodium sulphate and evaporated under reduced pressure.

8.8 g of the ester (R)-(+)-(II) are obtained and added to 16 ml of hexane, the mixture then being maintained at −24° C. After 24 hours 5.4 g of a solid phase separate, consisting of the substantially raceme ester (II), with $[\alpha]_D^{25} = -0.4°$ (C=1, CHCl$_3$). After evaporating the hexane from the supernatant under reduced pressure, 3.4 g of (R)-(+)-(II) are obtained, with $[\alpha]_D^{25} = +8.2°$ (C=1, CHCl$_3$), e.e. = 95% and yield = 17.0%.

EXAMPLE 2 a) hydrolysis of (R,S)-(II) with PS lipase in phosphate buffer/dioxane 20 g of (R,S)-benzoyl-1,2-isopropylideneglycerol (II) were added to a solution of 15 g of Amano PS lipase in 300 ml of pH 7, 0.01N phosphate buffer and 100 ml of dioxane.

The reaction was conducted as described in Example 1a. After 11 hours the reaction was halted at 50% conversion, obtaining 9.4 g of (S)-(−)-(II), with $[\alpha]_D^{25} = -5.4°$ (C=1, CHCl$_3$) and e.e. = 63%, and 5.3 g of (S)-(+)-(I), with $[\alpha]_D^{25} = +7.1°$ (C=1, MeOH), and e.e. = 62%.

b) Crystallization of (II)

The crystallization procedure described in Example 1b) is used to obtain 5.9 g of (S)-(−)-(II), with $[\alpha]_D^{25} = -8.0°$ (C=1, CHCl$_3$), e.e. = 93%, yield = 29.5%, 5.6 g of (R)-(+)-(II), with $[\alpha]_D^{25} = +8.2°$ (C=1, CHCl$_3$), e.e. = 95%, yield = 28.0%, and 6.9 g of (R,S)-(II) which can be recycled to the enzymatic hydrolysis reaction.

EXAMPLE 3 a) hydrolysis of (R,S)-(II) with lipase in phosphate buffer/isopropyl ether 20 g of (R,S)-benzoyl-1,2-isopropylideneglycerol (II) were added to a solution of 15 g of Amano PS lipase in 300 ml of pH 7, 0.01N phosphate buffer and 100 ml of isopropyl ether.

The reaction was conducted as described in Example 1a. After 18 hours the reaction was halted at 50% conversion, obtaining 9.6 g of (S)-(−)-(II), with $[\alpha]_D^{25} = -5.0°$ (C=1, CHCl$_3$) and e.e. = 60%, and 5.3 g of (S)-(+)-(I), with $[\alpha]_D^{25} = +6.8°$ (C=1, MeOH), and e.e. = 59%.

b) Crystallization of (II)

The crystallization procedure described in Example 1b) is used to obtain 5.8 g of (S)-(−)-(II), with $[\alpha]_D^{25} = -8.2°$ (C=1, CHCl$_3$), e.e.=95%, yield=29.0%, 5.3 g of (R)-(+)-(II), with $[\alpha]_D^{25} = +8.1°$ (C=1, CHCl$_3$), e.e.=94%, yield=26.6%, and 7.6 g of (R,S)-(II) which can be recycled to the enzymatic hydrolysis reaction.

EXAMPLE 4 a) hydrolysis of (R,S)-(II) with OF lipase in buffer solution 20 g of (R,S)-benzoyl-1,2-isopropylideneglycerol (II) were added to a solution of 1.0 g of OF lipase in 400 ml of pH 7, 0.01N phosphate buffer at 30° C.

The reaction was conducted as described in Example 1a. After 30 minutes the reaction was halted at 50% conversion, obtaining 9.5 g of (S)-(−)-(II), with $[\alpha]_D^{25} = -1.4°$ (C=1, CHCl$_3$) and e.e.=16%, and 5.4 g of (S)-(+)-(I), with $[\alpha]_D^{25} = +1.9°$ (C=1, MeOH), and e.e.=17%.

b) Crystallization of (II)

The crystallization procedure described in Example 1b) is used to obtain 1.5 g of (S)-(−)-(II), with $[\alpha]_D^{25} = -8.1°$ (C=1, CHCl$_3$), e.e.=94%, yield=7.5%, 1.6 g of (R)-(+)-(II), with $[\alpha]_D^{25} = +8.0°$ (C=1, CHCl$_3$), e.e.=93%, yield=8.0%, and 15.6 g of (R,S)-(II) which can be recycled to the enzymatic hydrolysis reaction.

EXAMPLE 5 a) hydrolysis of (R,S)-(II) with OF lipase in phosphate buffer/methyl tert-butyl ether 20 g of (R,S)-benzoyl-1,2-isopropylideneglycerol (II) were added to a solution of 1.0 g of OF lipase in 350 ml of pH 7, 0.01N phosphate buffer and 50 ml of methyl tert-butyl ether.

The reaction was conducted as described in Example 1a. After 30 minutes the reaction was halted at 50% conversion, obtaining 9.5 g of (S)-(−)-(II), with $[\alpha]_D^{25} = -3.3°$ (C=1, CHCl$_3$) and e.e.=39%, and 5.3 g of (S)-(+)-(I), with $[\alpha]_D^{25} = +4.5°$ (C=1, MeOH), and e.e.=39%.

b) Crystallization of (II)

The crystallization procedure described in Example 1b) is used to obtain 37 g of (S)-(−)-(II), with $[\alpha]_D^{25} = -8.2°$ (C=1, CHCl$_3$), e.e.=95%, yield=18.5%, 3.5 g of (R)-(+)-(II), with $[\alpha]_D^{25} = +8.0°$ (C=1, CHCl$_3$), e.e.=93%, yield=17.5%, and 11.3 g of (R,S)-(II) which can be recycled to the enzymatic hydrolysis reaction.

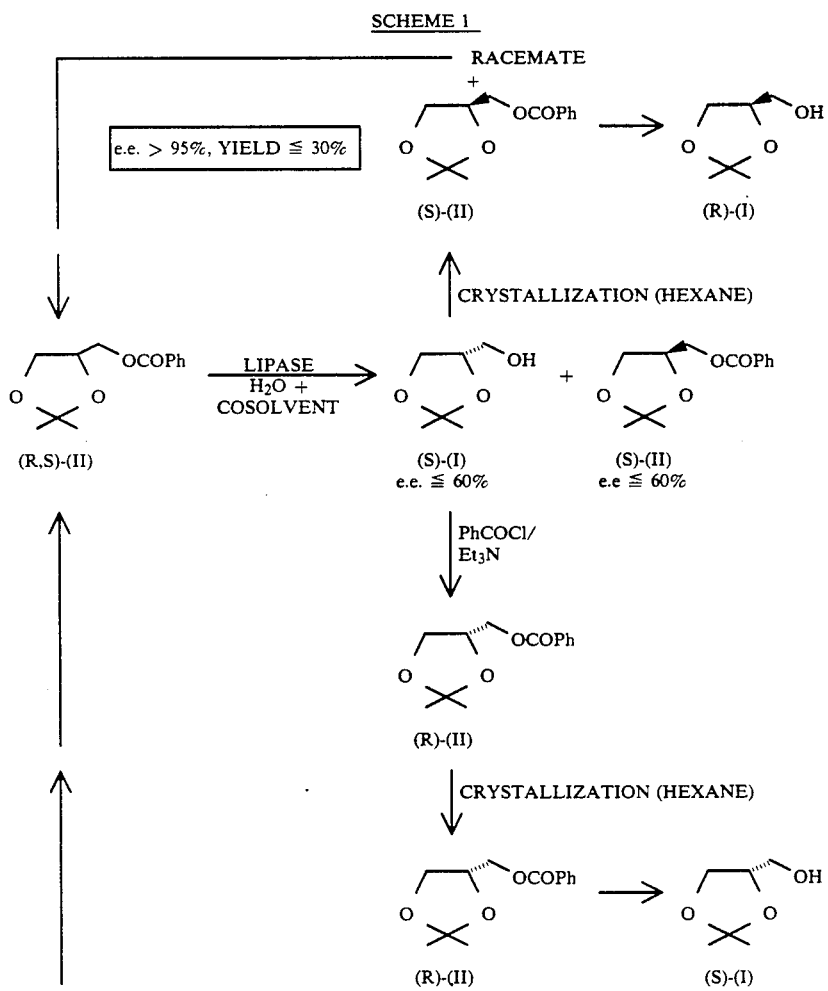

SCHEME 1

SCHEME 1

-continued

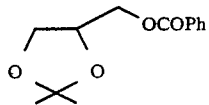

+

└────────── RACEMATE

We claim:
1. A process for separating the optical isomers from a racemic mixture of 1,2-isopropylideneglycerol benzoyl ester of the formula (II):

$$\text{\reflectbox{}}$$

comprising the steps of:
(a) hydrolyzing partially, enantioselectively and enzymatically 1,2-isopropylideneglycerol benzoyl ester of the formula (II), wherein said hydrolysis is catalyzed by a free or immobilized lipase in an aqueous buffered solution, with a cosolvent selected from the group consisting of linear aliphatic ethers, branched aliphatic ethers and heterocyclic ethers;
(b) separating the (S) enantiomerically enriched benzoyl ester (II) fraction from the (S) enantiomerically enriched alcohol; and
(c) crystallizing (R,S) benzoyl ester (II) in racemic form from the (S) enantiomerically enriched benzoyl ester fraction derived in step (b) from $C_5$–$C_8$ aliphatic hydrocarbons which leaves, predominately, the selectively obtained (S) enantiomer of the benzoyl ester (II) in the mother liquor.

2. The process according to claim 1 further comprising:
(a') esterifying the (S) enantiomerically enriched alcohol derived from step (b) to produce the (R) enantiomerically enriched benzoyl ester of formula (II); and
(b') crystallizing (R,S) benzoyl ester (II) in racemic form from the (R) enantiomerically enriched alcohol derived in step (a') from $C_5$–$C_8$ aliphatic hydrocarbons which leaves, predominately, the selectively obtained (R) enantiomer (II) in the mother liquor.

3. A process as claimed in claim 1, wherein the crystallization solvent is hexane.

4. A process as claimed in claim 1 or 2, wherein the crystallization is conducted by dispersing the ester (II) in the solvent and cooling to −24° C. for 24 hours.

5. A process as claimed in claim 1 or 2, wherein the ester (II):solvent weight ratio is between 1:4 and 1:1.

6. A process as claimed in claim 5, wherein the ester (II):solvent weight ratio is 1:2.

7. A process as claimed in claim 1, wherein the aliphatic ether used as cosolvent is diisopropylether or methyl tert-butyl ether.

8. A process as claimed in claim 1, wherein the heterocyclic ether used as cosolvent is dioxane or tetrahydrofuran.

9. A process as claimed in claim 1 or 2, wherein the quantity of cosolvent used varies from 5 to 50% v/v of the buffer solution.

10. A process as claimed in claim 9, wherein the quantity of cosolvent used varies from 10 to 25% v/v of the buffer solution.

11. A process as claimed in claim 1 or 2, wherein the enzymatic hydrolysis reaction is conducted at a temperature of between 15° and 40° C.

12. A process as claimed in claim 11, wherein the enzymatic hydrolysis reaction is conducted at a temperature of between 25° and 35° C.

13. A process as claimed in claim 1, wherein the substrate (II) is used in a concentration of between 1 and 10% by weight.

14. A process as claimed in claim 13, wherein the substrate (II) is used in a concentration of 5% by weight.

15. A process as claimed in claim 1, wherein the enzymes used are *Pseudomonas cepacea* and *Candida cylindracea* lipases.

16. A process as claimed in claim 15, wherein the enzyme is used in a weight ratio to the substrate (II) of between 1/100 and 1/1.

* * * * *